United States Patent
Goto

(10) Patent No.: US 12,354,333 B2
(45) Date of Patent: Jul. 8, 2025

(54) LEARNING DEVICE, OPERATION METHOD OF LEARNING DEVICE, AND MEDICAL IMAGE PROCESSING TERMINAL

(71) Applicant: FUJIFILM Corporation, Tokyo (JP)

(72) Inventor: Misaki Goto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 327 days.

(21) Appl. No.: 17/930,911

(22) Filed: Sep. 9, 2022

(65) Prior Publication Data

US 2023/0084954 A1 Mar. 16, 2023

(30) Foreign Application Priority Data

Sep. 10, 2021 (JP) ................................. 2021-148137

(51) Int. Cl.
*G16H 30/40* (2018.01)
*G06T 7/00* (2017.01)
*G06V 10/774* (2022.01)
*G16H 15/00* (2018.01)

(52) U.S. Cl.
CPC .......... *G06V 10/774* (2022.01); *G06T 7/0012* (2013.01); *G16H 15/00* (2018.01); *G16H 30/40* (2018.01); *G06T 2207/20081* (2013.01); *G06T 2207/30096* (2013.01); *G06V 2201/03* (2022.01)

(58) Field of Classification Search
None
See application file for complete search history.

(56) References Cited

U.S. PATENT DOCUMENTS

| | | | |
|---|---|---|---|
| 2013/0223589 A1* | 8/2013 | Fujisawa | A61B 6/488 378/19 |
| 2016/0027175 A1* | 1/2016 | Kim | G06T 7/0016 382/131 |
| 2019/0005354 A1 | 1/2019 | Nakamura | |
| 2019/0057503 A1 | 2/2019 | Nakamura | |
| 2020/0090382 A1* | 3/2020 | Huang | G06N 3/084 |
| 2020/0118265 A1 | 4/2020 | Igarashi | |
| 2020/0126217 A1 | 4/2020 | Minami | |

(Continued)

FOREIGN PATENT DOCUMENTS

| | | | | |
|---|---|---|---|---|
| CN | 107194158 | * | 9/2017 | ............. G06F 19/00 |
| CN | 109785300 | * | 5/2019 | ............... G06N 3/04 |

(Continued)

OTHER PUBLICATIONS

An Office Action; "Notice of Reasons for Refusal," mailed by the Japanese Patent Office on May 27, 2025, which corresponds to Japanese Patent Application No. 2021-148137 and is related to U.S. Appl. No. 17/930,911; with English language translation.

*Primary Examiner* — Beniyam Menberu
(74) *Attorney, Agent, or Firm* — Studebaker Brackett PLLC

(57) ABSTRACT

A standard image is extracted from a still image group or a moving image associated with medical test report data stored in a database, using the medical test report data. A frame image group is created from the still image group or the moving image that configures the standard image, a learning candidate image data set is extracted from the frame image group based on the standard image, and training data is sorted out from the learning candidate data set. Learning is performed using the training data which is sorted out.

10 Claims, 15 Drawing Sheets

(56) References Cited

U.S. PATENT DOCUMENTS

| | | | | |
|---|---|---|---|---|
| 2021/0256295 A1* | 8/2021 | Matsumoto | .......... | G06V 10/809 |
| 2021/0365744 A1* | 11/2021 | Navarrete Michelini | .................. | |
| | | | | G06V 10/82 |
| 2022/0180194 A1* | 6/2022 | Bae | ........................ | G06N 3/096 |
| 2022/0335613 A1* | 10/2022 | Wang | .................... | G06T 7/0012 |
| 2023/0085203 A1* | 3/2023 | Cao | ....................... | G06T 11/005 |
| | | | | 382/131 |

FOREIGN PATENT DOCUMENTS

| | | | | | |
|---|---|---|---|---|---|
| JP | 2019-010411 A | | 1/2019 | | |
| JP | 2019-033924 A | | 3/2019 | | |
| JP | 2019-118694 A | | 7/2019 | | |
| JP | 2020-058590 A | | 4/2020 | | |
| JP | 2020-064476 A | | 4/2020 | | |
| JP | 2020103516 | * | 7/2020 | .............. | A61B 6/00 |
| JP | 2020-154630 A | | 9/2020 | | |
| KR | 102043672 | * | 11/2019 | .............. | A61B 5/00 |
| KR | 20210099411 | * | 8/2021 | .............. | A61B 5/107 |
| KR | 20220103852 | * | 7/2022 | .............. | G16H 30/40 |

\* cited by examiner

LEARNING DEVICE, OPERATION METHOD OF LEARNING DEVICE, AND MEDICAL IMAGE PROCESSING TERMINAL

CROSS-REFERENCE TO RELATED APPLICATIONS

This application claims priority under 35 U.S.C § 119(a) to Japanese Patent Application No. 2021-148137 filed on 10 Sep. 2021. The above application is hereby expressly incorporated by reference, in its entirety, into the present application.

BACKGROUND OF THE INVENTION

1. Field of the Invention

The present invention relates to a learning device, an operation method of a learning device, and a medical image processing terminal.

2. Description of the Related Art

In the medical field, machine learning is increasingly used to learn lesion detection, lesion type classification, site determination, and the like to support doctor's diagnosis, but a large amount of data is necessary in machine learning. Therefore, by automatically acquiring data from a system provided in a hospital and adding the data to learning, further improvement in learning accuracy is expected in a short period of time. However, in a case where all the acquired data is used in learning, there is a possibility of learning the wrong type of data that is not to be used in the first place, data that is unsuitable for learning which is not a system operation target, and the like, and rather a decrease in accuracy is conceivable. Therefore, by using a test report generated for each test to acquire data, necessary data can be extracted with high accuracy.

Specifically, in JP2020-154630A, electronic medical record information matching the history of designated medical treatment content is acquired from a database that manages electronic medical record information indicating a record of medical treatment content for each patient, and a medical image specified in an interpretation report associated with the acquired electronic medical record information is collected. In JP2019-33924A (corresponding to US2019/057503A1), in a case where a medical image corresponding to an interpretation report searched from a keyword is acquired and an anatomical region associated with a search keyword extracted from the medical image is different in terms of a standard size or a standard shape of the anatomical region, information indicating the anatomical region and the medical image are registered as correct data.

SUMMARY OF THE INVENTION

An image having a designated feature is collected from the interpretation report associated with an electronic medical record matching the history of medical treatment content in JP2020-154630A, and a medical image which is different in terms of the standard size or the standard shape of the anatomical region is registered from the interpretation report searched by the keyword in JP2019-33924A. An image to be used in learning is acquired from images published in a report in JP2020-154630A and JP2019-33924A, but in this case, it is difficult or inefficient to acquire a large number of images necessary for learning in some cases. For this reason, it is required to automatically acquire images necessary for learning from a large number of frames configuring an endoscope or ultrasound test motion picture or the like or a large number of images stored in the database with high accuracy at which data is extracted from a test report.

An object of the present invention is to provide a learning device, an operation method of a learning device, and a medical image processing terminal that acquire appropriate information from report information and extract data to be used in learning.

According to an aspect of the present invention, there is provided a learning device comprising a processor. The processor extracts a standard image from a still image group or a moving image associated with medical test report data stored in a database, using the medical test report data, sorts out training data from a frame image group configuring the still image group or the moving image associated with the medical test report data, using the standard image, and performs learning using the training data.

It is preferable that the processor extracts a learning candidate data set from the standard image and sorts out the training data from the learning candidate data set.

It is preferable the processor extracts, as the learning candidate data set, an image group acquired within a time range determined in advance from a time, at which the standard image is acquired, from the frame image group configuring the still image group or the moving image associated with the medical test report data.

It is preferable that the processor extracts the standard image based on lesion information from the still image group or the moving image associated with the medical test report data.

It is preferable that the processor extracts at least any one of an image without findings of the medical test report data, an image that does not have a lesion, or an image of a benign lesion as the standard image.

It is preferable that the processor extracts, from the still image group or the moving image associated with the medical test report data, the standard image based on at least any one of lesion information, findings information, image quality information, site information, organ information, a treatment method, or a specific keyword, which is information linked with the medical test report data.

It is preferable that the processor inputs the still image group or the moving image associated with the medical test report data into a trained model, and extracts the standard image using an inference result of machine learning in which the trained model is used.

It is preferable that the processor displays, on a display, at least any one of the still image group or the moving image associated with the medical test report data and extracts the standard image by user selection.

It is preferable that the processor sorts out, as the training data, an image that does not have a lesion or an image of a benign lesion from the learning candidate data set using the standard image.

It is preferable that the processor sorts out, as the training data, at least any one of an image including the same site, an image including the same organ, an image having image correlation which is equal to or larger than a certain value, or an image having the same inference result of machine learning with respect to the standard image from the learning candidate data set.

It is preferable that the processor sorts out, as the training data, an image that has image correlation, which is equal to or smaller than a certain value, with respect to a peripheral frame image instead of sorting out using the standard image from the learning candidate data set.

According to another aspect of the present invention, there is provided an operation method of a learning device comprising a step of extracting a standard image from a still image group or a moving image associated with medical test report data stored in a database, using the medical test report data, a step of sorting out training data from a frame image group configuring the still image group or the moving image associated with the medical test report data, using the standard image, and a step of performing learning using the training data.

According to still another aspect of the present invention, there is provided a medical image processing terminal comprising a processor. The processor extracts a standard image from a still image group or a moving image associated with medical test report data stored in a database, using the medical test report data, and sorts out training data from a frame image group configuring the still image group or the moving image associated with the medical test report data, using the standard image, and stores the training data.

Appropriate information can be acquired from report information, and data necessary for using in learning can be extracted.

DESCRIPTION OF THE PREFERRED EMBODIMENTS

Figure 1:
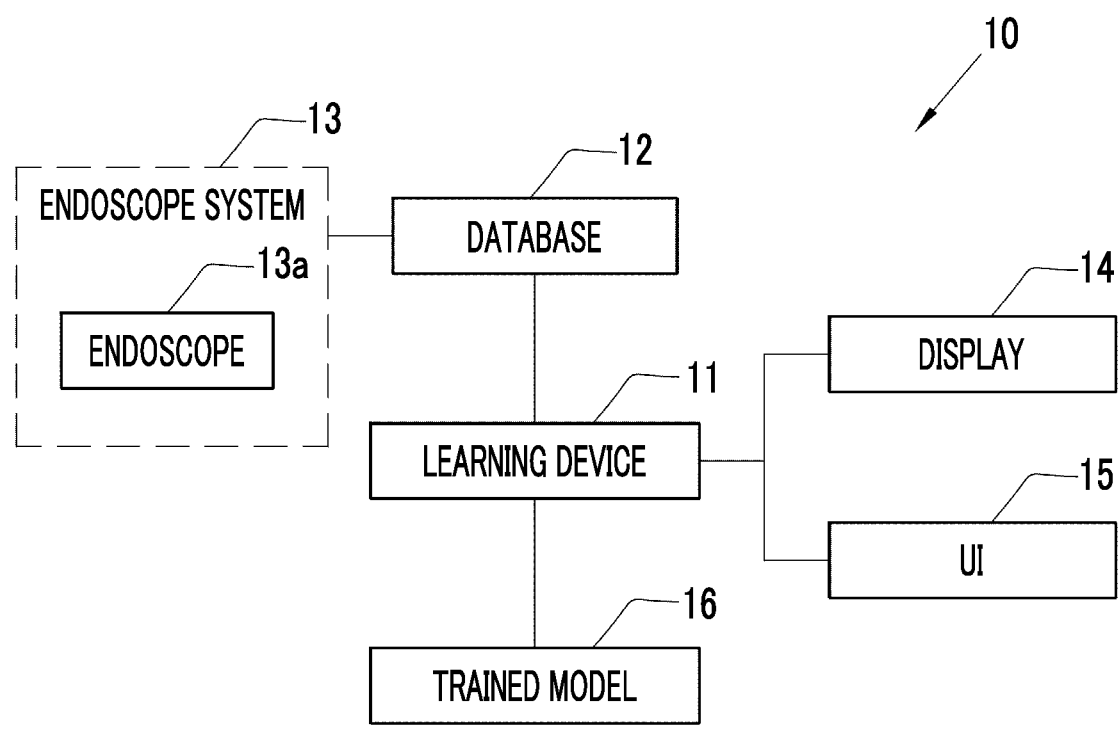
FIG. 1 is an explanatory diagram showing connection apparatuses of a learning device.

FIG. 1 is a diagram showing a configuration example of a learning system 10 according to an embodiment of the present invention. The learning system 10 has a learning device 11, a database 12, an endoscope system 13 having an endoscope 13a, a display 14, a user interface 15, and a trained model 16. The learning device 11 is electrically connected to the database 12, the endoscope system 13, the display 14, the user interface 15, and the trained model 16.

The database 12 is a device that stores an acquired image and that can transmit and receive data to and from the learning device 11 and may be a recording medium such as a universal serial bus (USB) and a hard disc drive (HDD). The user interface 15 is an input device that performs a setting input into the learning device 11 and includes a keyboard and a mouse. The trained model 16 infers a still image group or a moving image input from the learning device 11 through machine learning and outputs an inference result according to set content.

The database 12 stores medical test reports and medical images created by the endoscope system 13 and other medical devices. In a case where imaging of a medical test is not particularly designated, white light is used as illumination light, a video signal of a 60-frame image (60 frame per second (fps)) is acquired per second, and an imaging time is recorded. In addition, it is preferable to count a time point per $1/100$ seconds in a case where the video signal is 60 fps.

Figure 2:
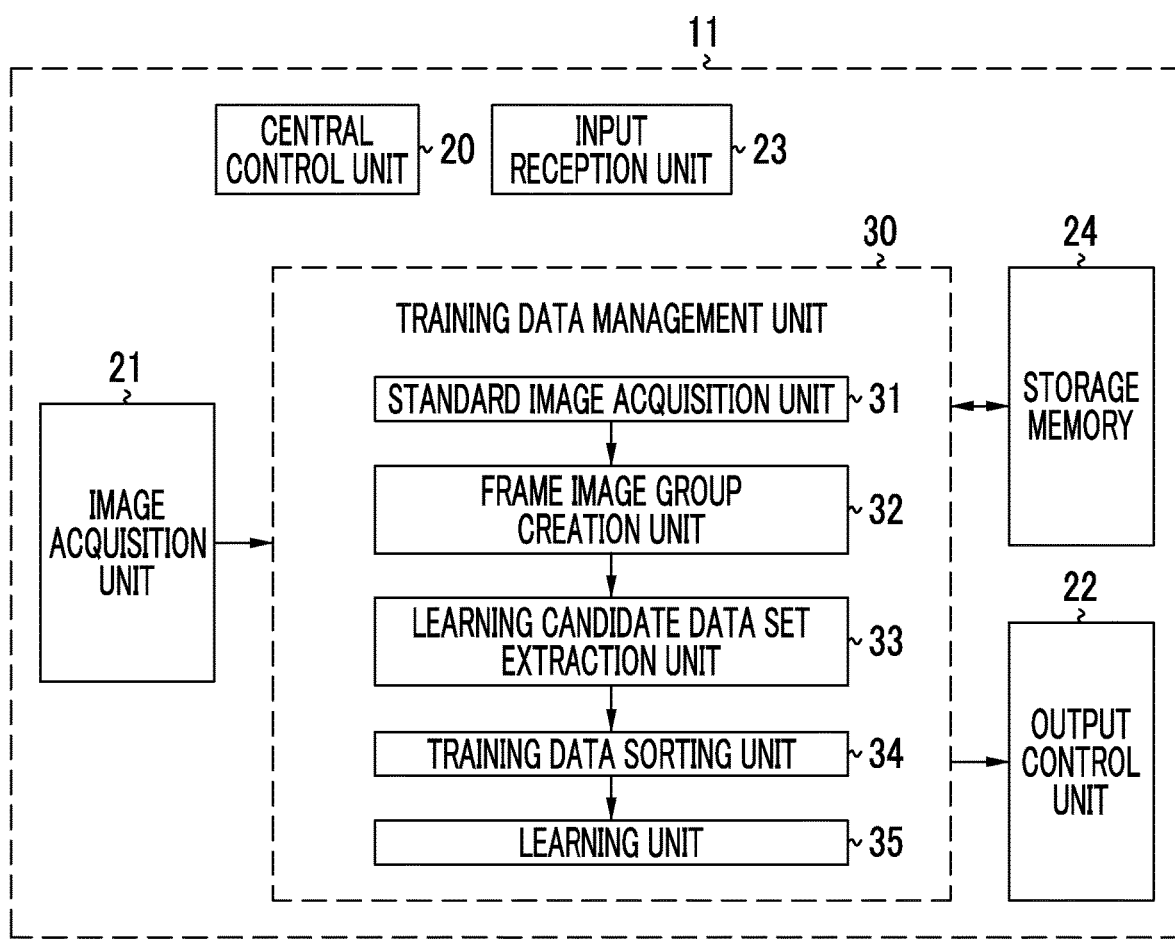
FIG. 2 is a block diagram showing a function of the learning device.

As shown in FIG. 2, in the learning device 11, functions of an image acquisition unit 21, an output control unit 22, an input reception unit 23, a storage memory 24, and a training data management unit 30 are realized as a program in a program memory is operated by a central control unit 20 composed of an image control processor. In addition, with the realization of a function of the training data management unit 30, functions of a standard image acquisition unit 31, a frame image group creation unit 32, a learning candidate data set extraction unit 33, a training data sorting unit 34, and a learning unit 35 are realized. The image acquisition unit 21 receives data such as an image stored in the database 12.

The output control unit 22 performs control of causing the display 14 to display a still image or a motion picture and transmits the still image group or the moving image for inference to the trained model 16. The input reception unit 23 connects to the user interface 15. The storage memory 24 temporarily stores an image edited and extracted by the training data management unit 30. For temporary storage, the database 12 may have the function instead of the storage memory 24. A program related to processing such as image processing is stored in the program memory (not shown) in the learning device 11. The trained model 16 is a computer algorithm that consists of a neural network performing machine learning, classifies the still image group or the moving image input according to learning content, and infers detection of a specific image.

The output control unit 22 performs control of displaying a still image or a motion picture on the display 14. Extraction of a standard image 50 and sorting-out of training data 53 are displayed on the screen in a case of being performed by a user operation. The output control unit may be used in checking a medical test report 40, a diagnosis image 41, a report-published image 42, a report-non-published image 43, and a test moving image 44, on which sorting and extraction are not performed and which are stored in the database 12. In addition, the output control unit transmits an image input in a case of making inference through machine learning by the trained model 16.

Figure 3:
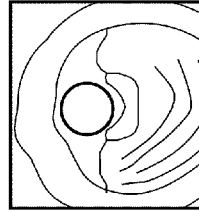
FIG. 3 is an explanatory diagram showing a medical test report.

As shown in FIG. 3, the medical test report 40 includes at least the diagnosis image 41 indicating a test result and doctor's findings in a medical test. The medical test report 40 is a summary of a result of the medical test, which is created by a doctor, and includes performed medical test information, patient information, report creator information, report creation date and time, findings information, and the diagnosis image 41 to support a diagnostic result of the medical test. The image quality of the diagnosis image 41 published in the medical test report 40 is good, and an image in which the presence or absence of a region-of-interest R such as a lesion is clear is mainly used.

Figure 4:
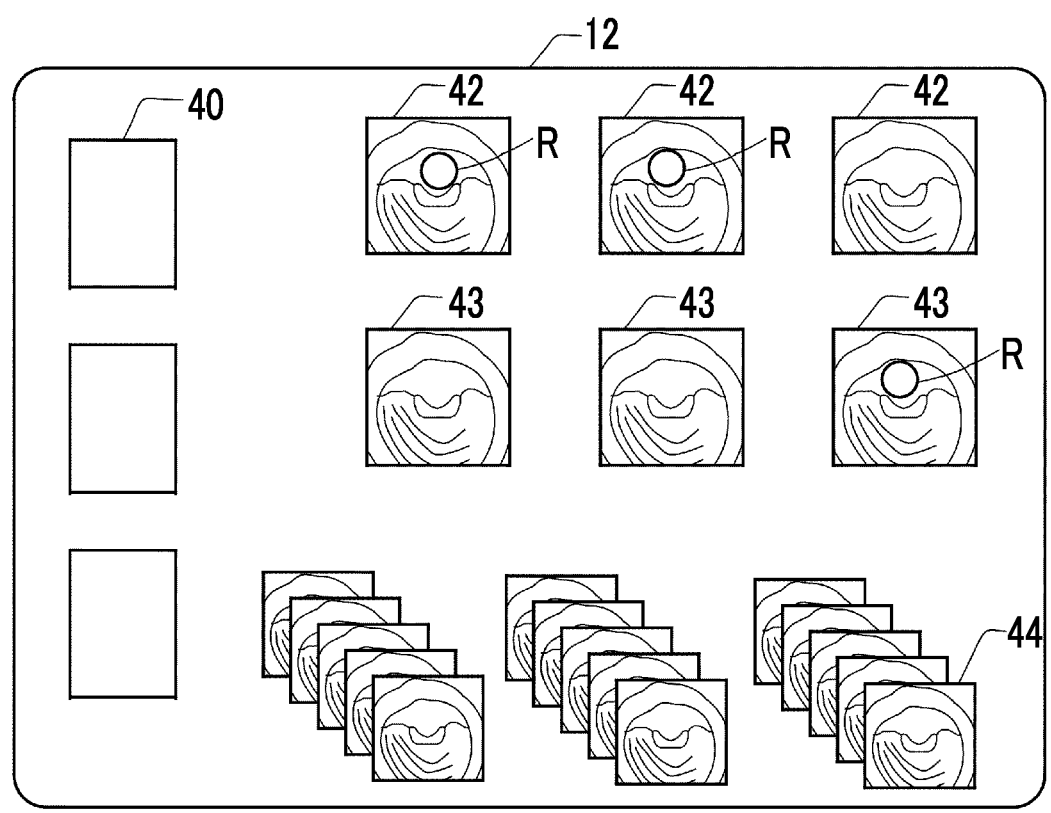
FIG. 4 is an explanatory diagram showing data stored in a database.

As shown in FIG. 4, the database 12 stores data of the medical test report 40, the report-published image 42, the report-non-published image 43, and the test moving image 44 in a file. It is preferable that the medical test report 40 is tagged with data such as test information, findings, and image information of the diagnosis image 41 used as keywords. The report-published image 42 is an image of raw data before editing such as changing an image size in report publication of the diagnosis image 41, that is, a still image adopted in publication of the medical test report 40. The report-non-published image 43 is a still image that is a candidate for the diagnosis image 41 and is not adopted in publication of the medical test report 40. The test moving image 44 is a moving image picked up in a medical test such as an endoscope test. The report-published image 42 and the report-non-published image 43 are captured images acquired by being captured during a medical test or frame images extracted from the test moving image 44. To distinguish between the report-published image 42 and the report-non-published image 43, it is preferable to add image information such as "report publication" to a still image selected as the diagnosis image 41 in a case of creating the medical test report 40.

Data files stored in the database 12 are associated with each other. Specifically, the report-published image 42, the report-non-published image 43, and the test moving image 44 also retain information such as a test ID, a patient ID, and date and time at which a test was performed as shown in FIG. 3. It is preferable that the information is automatically set in a case of imaging a medical test. Accordingly, the medical test report 40 can specify the report-published image 42 which is the basis of the diagnosis image 41 from the test ID and the patient ID and the report-non-published image 43 and the test moving image 44, which are acquired through the same test. In addition, links and information between pieces of data of the same test may be retained. As described above, it is preferable that pieces of data before and after extracting and editing are associated with each other.

Further, the report-published image 42 and the report-non-published image 43 are captured images captured in a medical test or frame images extracted from the test moving image 44 and are linked with information of a medical test, findings, the presence or absence of a region-of-interest, such as a lesion, organ or site information, and information such as a treatment method. The captured image is a still image acquired as a doctor performs a capturing operation during the medical test and is an image that has a good image quality and is useful as an image used in a report or an image that has a high probability thereof.

Figure 17:
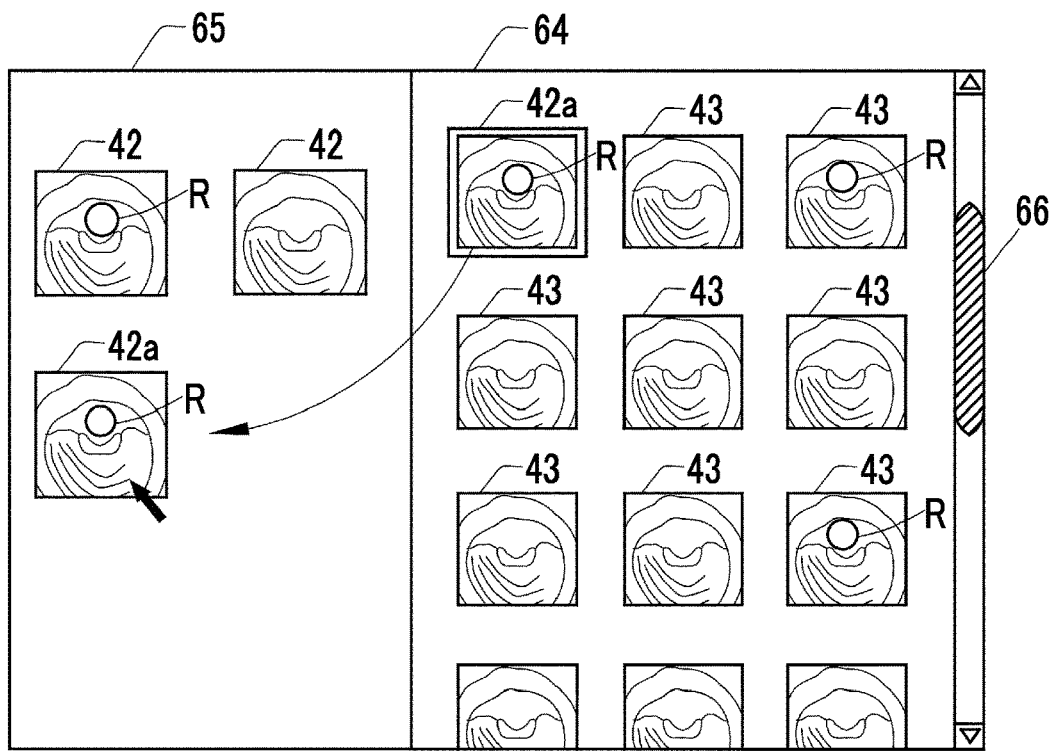
FIG. 17 is an explanatory diagram of selecting a report-published image from images acquired in a medical test.

FIG. 17 is an example of selecting the report-published image 42 from images acquired in a medical test. In image selection, an image selection region 64 for a report creator to select an image to be published in a report and an image display region 65 that displays the selected image as the report-published image 42 are displayed on the screen. The displayed image is a captured image or a frame image previously extracted from the test moving image 44. The report creator drags and drops, in the image display region 65, a report-published image 42a, which is determined to be able to be published in the report, from a large number of images displayed in the image selection region 64. Accordingly, the report-published image 42a is displayed and stored in the image display region 65. It is preferable to distinguish an image selected as the report-published image 42 from other images by displaying the selected image in a thick frame. In addition, in the image selection region 64, images can be further observed by operating a scroll bar 66, and the report-published image 42 can be selected. An unselected image is stored as the report-non-published image 43.

Figure 5:
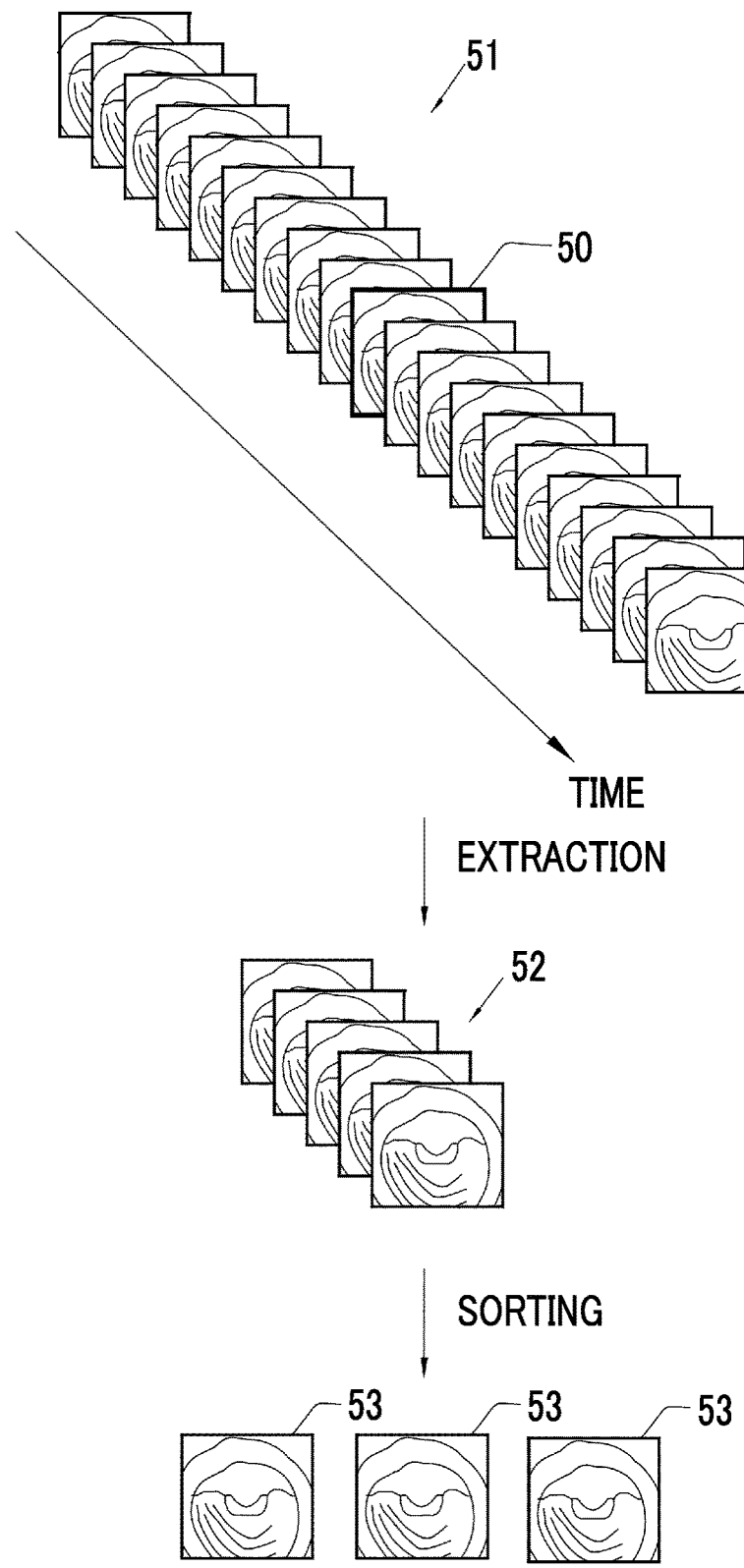
FIG. 5 is an explanatory diagram from extraction of a standard image to sorting-out of training data.

As shown in FIG. 5, in the training data management unit 30, the standard image 50, which is the basis of a learning image, is acquired by the standard image acquisition unit 31 from the database 12, and a frame image group 51 is created by the frame image group creation unit 32 from the test moving image 44 corresponding to the standard image 50. In addition, a learning candidate data set 52 is extracted by the learning candidate data set extraction unit 33 from the frame image group 51 based on a time range determined in advance, and the training data 53 is sorted out by the training data sorting unit 34 from the learning candidate data set 52. The training data 53 sorted out by the learning unit 35 is used in learning.

The standard image acquisition unit 31 extracts, from at least any one of the report-published image 42, the report-non-published image 43, or the test moving image 44 stored in the database 12, the standard image 50 to be used in sorting out the training data 53. The standard image 50 is an image that can be also used as the training data 53 and is determined by at least any one of findings content, lesion information, image information, a treatment method, a specific keyword, an inference result of machine learning, image correlation, or a user operation. It is preferable that the standard image 50 is an image that has a good image quality and does not have a lesion such as the region-of-interest R. The image information includes image quality information, site information, organ information, and region-of-interest R presence or absence information.

In extraction of the standard image 50, an image that does not have a lesion and has a good image quality is specified as a normal image from the database 12. The normal image is an image that is determined to have no lesion and no abnormality and to be normal in doctor's findings. A specifying method includes a method of narrowing down from information associated with an image, a method of using an inference result of machine learning, and a method in which a user makes visual determination and selection, and it is preferable to combine any one or a plurality of any of the methods and to extract the standard image 50. It is preferable to acquire a plurality of standard images 50.

Figure 6:
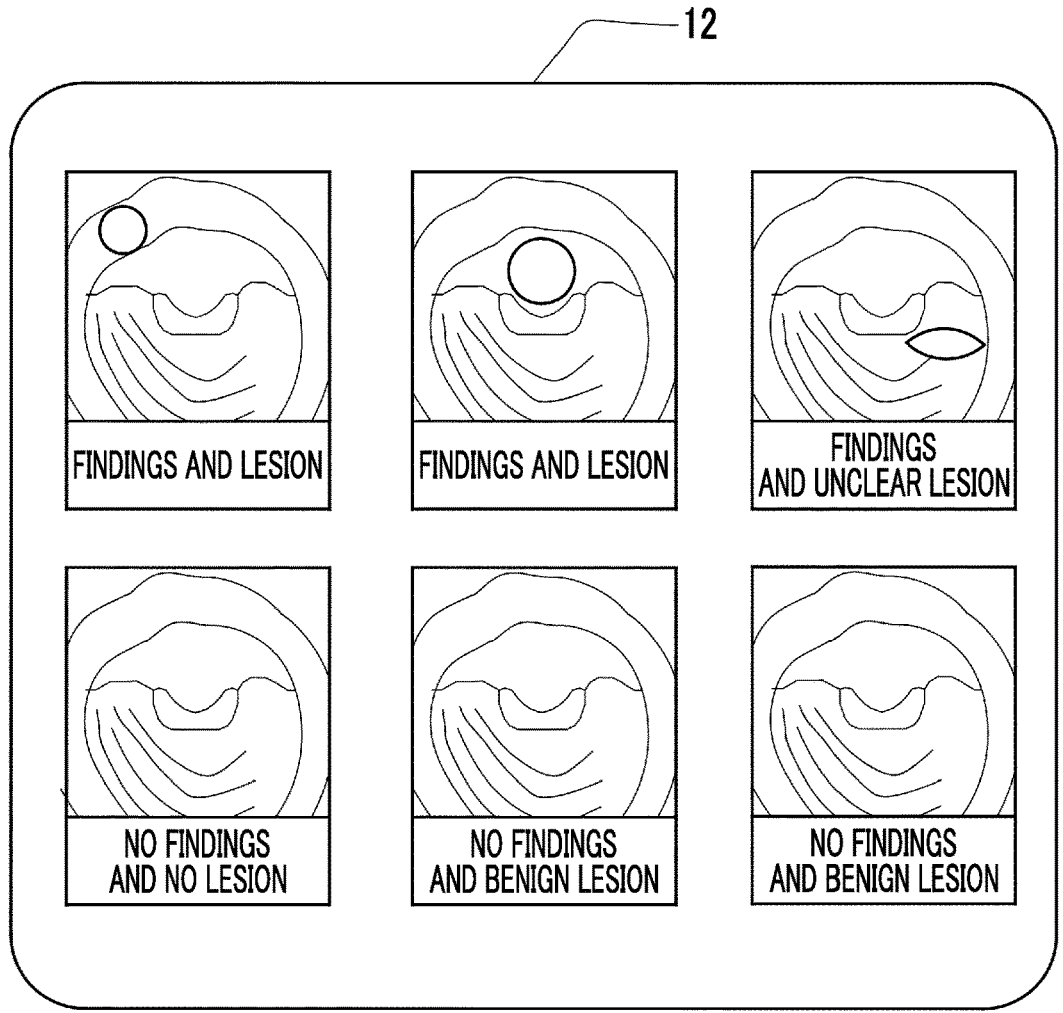
FIG. 6 is an explanatory diagram of extracting the standard image based on findings or lesion information.
Figure 6:
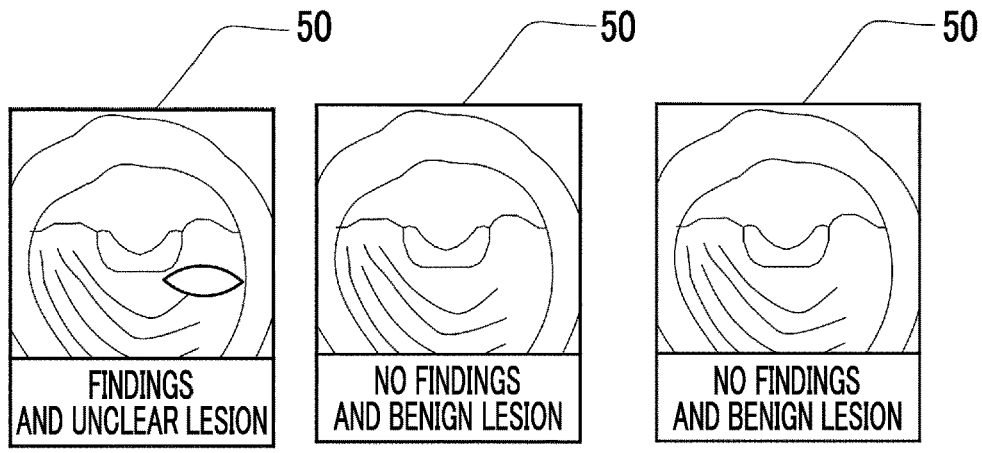

As shown in FIG. 6, in the method of narrowing down from information associated with an image, as the standard image 50, an image that does not have a lesion or an image of a benign lesion is extracted from lesion information and an image without findings is extracted from findings information. In addition to the findings information and the lesion information, the standard image 50 may be extracted from more detailed conditions. For example, the image quality information, the site information, the organ information, the treatment method, and the specific keyword are used. The report-published image 42 mainly has the findings information.

Figure 7:
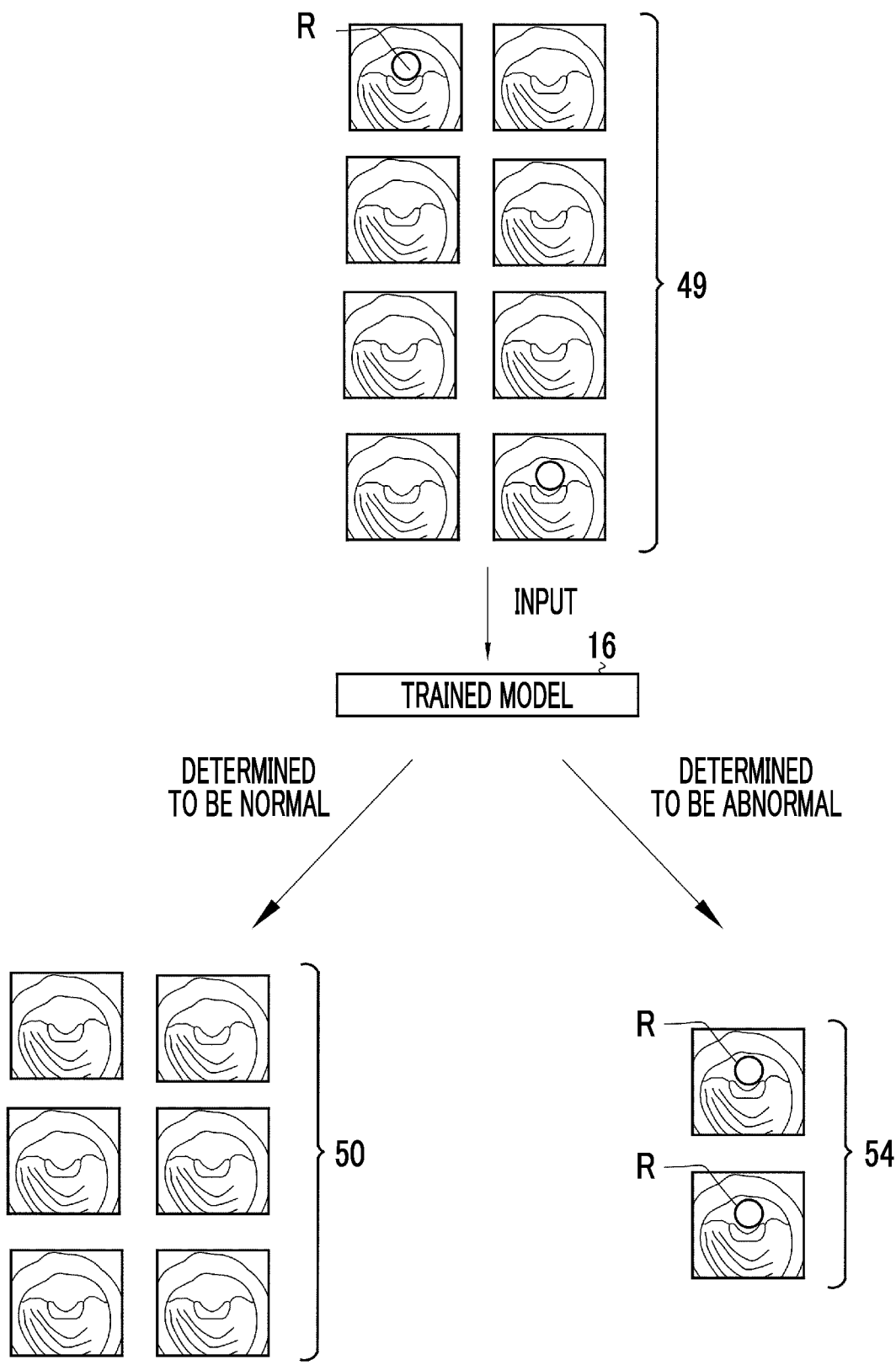
FIG. 7 is an explanatory diagram of extracting the standard image using an inference result of machine learning.

As shown in FIG. 7, in a method of using inference through machine learning, inference is made by inputting a database stored image group 49 from the database 12 into the trained model 16 which has previously learned a normal image via the learning device 11. The database stored image group 49 is composed of at least any one of frame images of the report-published image 42, the report-non-published image 43, and the test moving image 44. The inference is classifying whether or not the input image is normal, and in a case where the input image is normal, an image for which an inference result is obtained is extracted as the standard image 50. In addition, in a case where the input image is not normal, the image for which the result is obtained is defined as a non-adopted image 54 and is not used thereafter. In addition, it is preferable to add the inference result to the image information. The trained model 16 is a medical device different from the learning device 11, but may realize inference through machine learning as a part of the function of the learning device 11.

Figure 8:
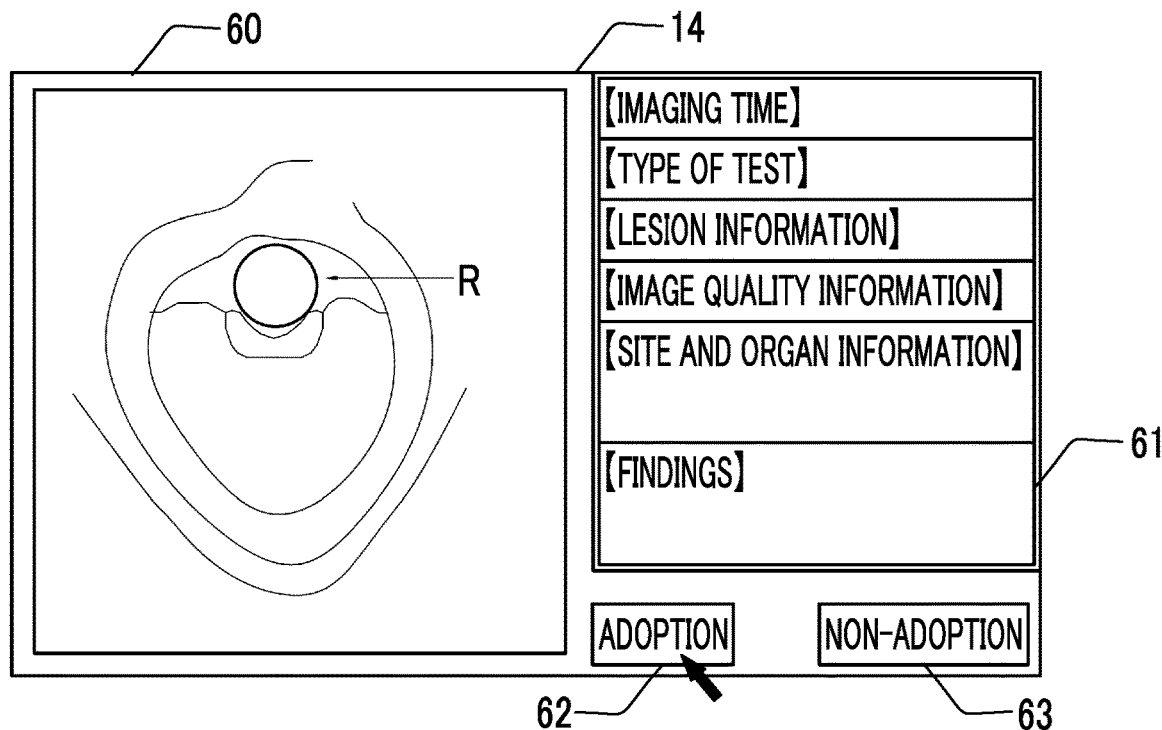
FIG. 8 is an explanatory diagram of extracting the standard image by user selection through screen display.

As shown in FIG. 8, in the method in which a user makes visual determination, an image display region 60, an image information display field 61, an adoption button 62, and a non-adoption button 63 are developed on the display 14, any one of the report-published image 42, the report-non-published image 43, or the test moving image 44 stored in the database 12 is displayed in the image display region 60, and image information which is an image or a moving image of the image display region 60 is displayed in the image information display field 61. The user determines an image suitable for the standard image 50 through image observation and image information checking. In a case where the displayed image is determined to be suitable for the standard image 50, the user selects the adoption button 62 to set as the standard image 50. In a case where the displayed image is determined to be not suitable, the non-adoption button 63 is selected. In a case of extracting from the test moving image 44, a scene suitable for the standard image 50 may be specified, and in a case where the adoption button 62 is selected, image extraction and storage may be performed.

Figure 9:
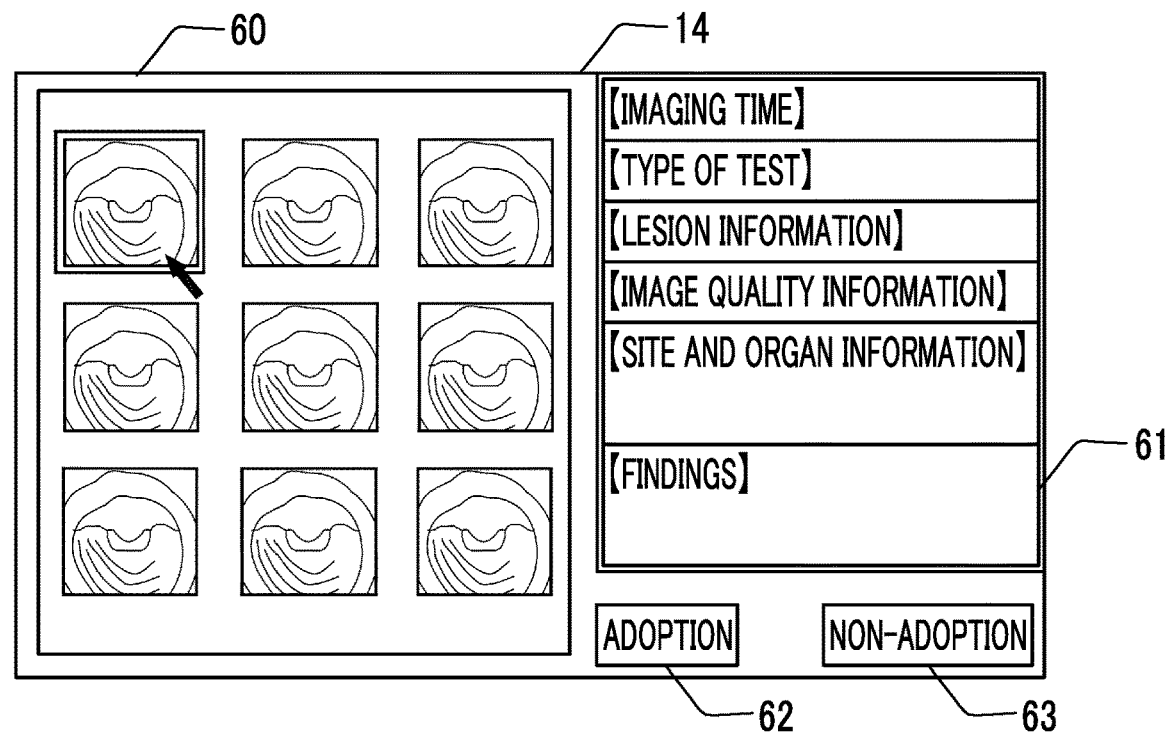
FIG. 9 is an explanatory diagram of extracting the standard image by user selection through thumbnail display.

As shown in FIG. 9, thumbnail display in which a plurality of images can be checked at once may be performed in the image display region 60. In this case, in a case of adopting as the standard image 50, the adoption button 62 is pressed after selecting a target image. In addition, in a case where the non-adoption button 63 is pressed with respect to the selected image, thumbnail display of an unselected image from the database 12 may be performed instead.

In a case where the standard image 50 is a frame image, the frame image group creation unit 32 creates the frame image group 51 based on the standard image 50. Specifically, the test moving image 44 configured by the frame image, which is the standard image 50, is specified from the database 12, and the frame image group 51 excluding an unnecessary portion from the test moving image 44 is created. For example, in a case where an imaging time of the test moving image 44 is long, it is preferable to perform division since the number of included image is enormous and to extract a moving image that has the frame image, which is the standard image 50, from a plurality of moving images after division. In addition, in a case where a scene that is not effective is determined in a test from image information such as a scene in which illumination light is turned off immediately after imaging start and immediately before imaging end of the test moving image 44, this portion is excluded, and a range effective in the test may be extracted. The test moving image 44 may be used as it is as the frame image group 51. The frame image group 51 is transmitted to the learning candidate data set extraction unit 33 together with the standard image 50. In a case where the standard image 50 is a captured image, the test moving image 44 acquired in the same test from a test ID is specified to extract an image, and the frame image group 51 is created.

The learning candidate data set extraction unit 33 acquires the learning candidate data set 52 from the frame image group 51 based on an imaging time of the standard image 50. Specifically, in the frame image group 51, an image group acquired within a time range determined in advance is extracted as the learning candidate data set 52 based on a time at which the standard image 50 is imaged. The acquired learning candidate data set 52 is transmitted to the training data sorting unit 34 together with the standard image 50.

Figure 10:
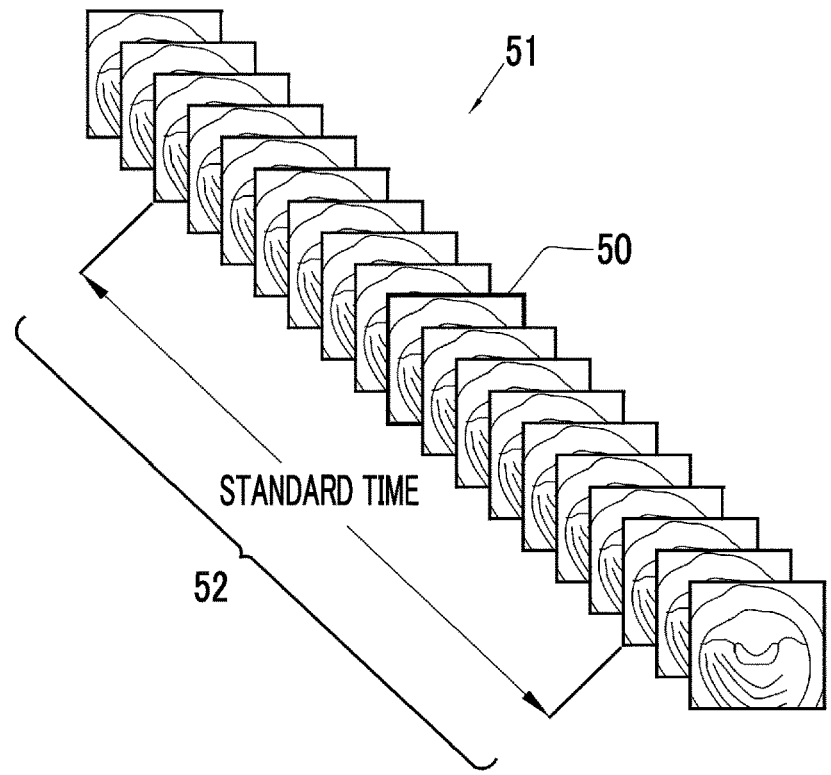
FIG. 10 is an explanatory diagram of extracting a learning candidate data set from a frame image group based on an imaging time of the standard image.

As shown in FIG. 10, the learning candidate data set 52 is extracted from an image group acquired within the time range determined in advance from a standard time, which is a time at which the standard image 50 is acquired. Within the time range determined in advance, it is preferable to set in the unit of one second from the standard time according to the necessary amount of the training data 53. Setting within the time range may be designated in detail by the user before extracting the standard image. Specifically, the user may previously set, according to an imaging situation, a range only before the standard time, a range only after acquiring the standard image 50, or a time range that is short before acquiring the standard image 50 and is long after the acquisition.

The training data sorting unit 34 sorts out an image having a high association with the standard image 50 in the image group configuring the learning candidate data set 52 as the training data 53. In the sorting method, images having common findings content, common lesion information, common image information, a common treatment method, and a common specific keyword and images having a similar inference result of machine learning and a similar calculation result of image correlation are sorted out. In addition to the training data 53, the standard image 50 is also transmitted to the learning unit 35. The sorted training data 53 may be transmitted and stored in the database 12.

Figure 11:
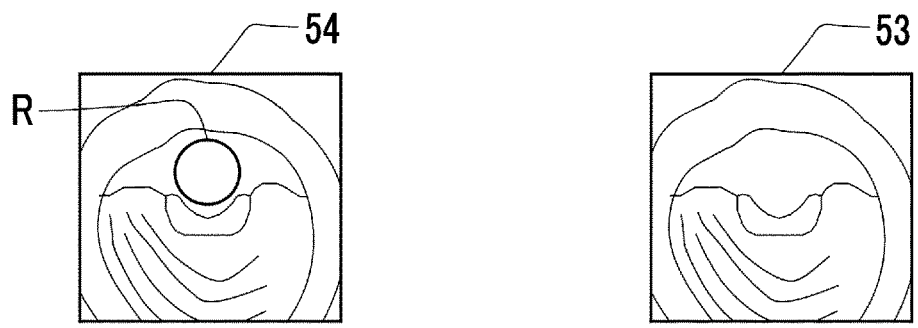
FIG. 11 is an explanatory diagram showing that the training data is a normal image.
Figure 11:
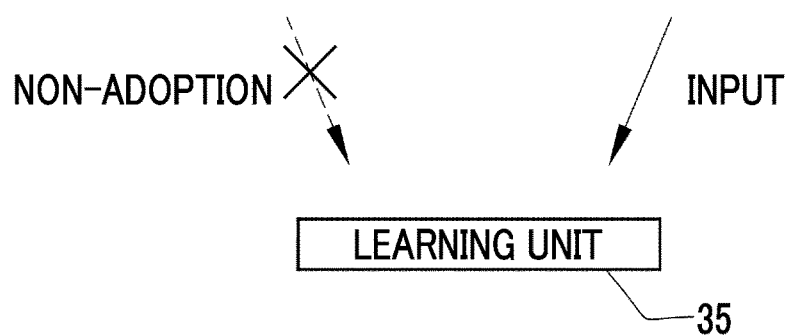

As shown in FIG. 11, the training data 53 that is transmitted to the learning unit 35 and is used in learning is a normal image that is determined to be normal in doctor's findings like the standard image 50, does not have a lesion or the like, and has a good image quality as well. The learning candidate data set 52 includes images acquired from the standard image 50 within the time range determined in advance and has a possibility that an image having a lesion is included since there are a large number of images. The training data 53 to be used in learning is sorted out from the learning candidate data set 52 acquired in large quantities. In order to perform sorting, there are methods of sorting by image information, a determination result of image correlation, and user selection. As a result of sorting, an image that has a lesion, such as the region-of-interest R, or an unclear place is the non-adopted image 54 and is not used in learning.

Since the training data 53 is a normal image that does not have a lesion, an image common to information that is included in the standard image and indicates being normal is acquired from the learning candidate data set 52. Specifically, data common to "no lesion" and "benign lesion" in lesion information is acquired from the learning candidate data set 52. In addition, in a case where an image configuring the learning candidate data set 52 excluding the standard image 50 has findings information, the training data 53 may be sorted out using content such as "no findings", "no lesion", and "no abnormality" in the findings information.

Figure 12:
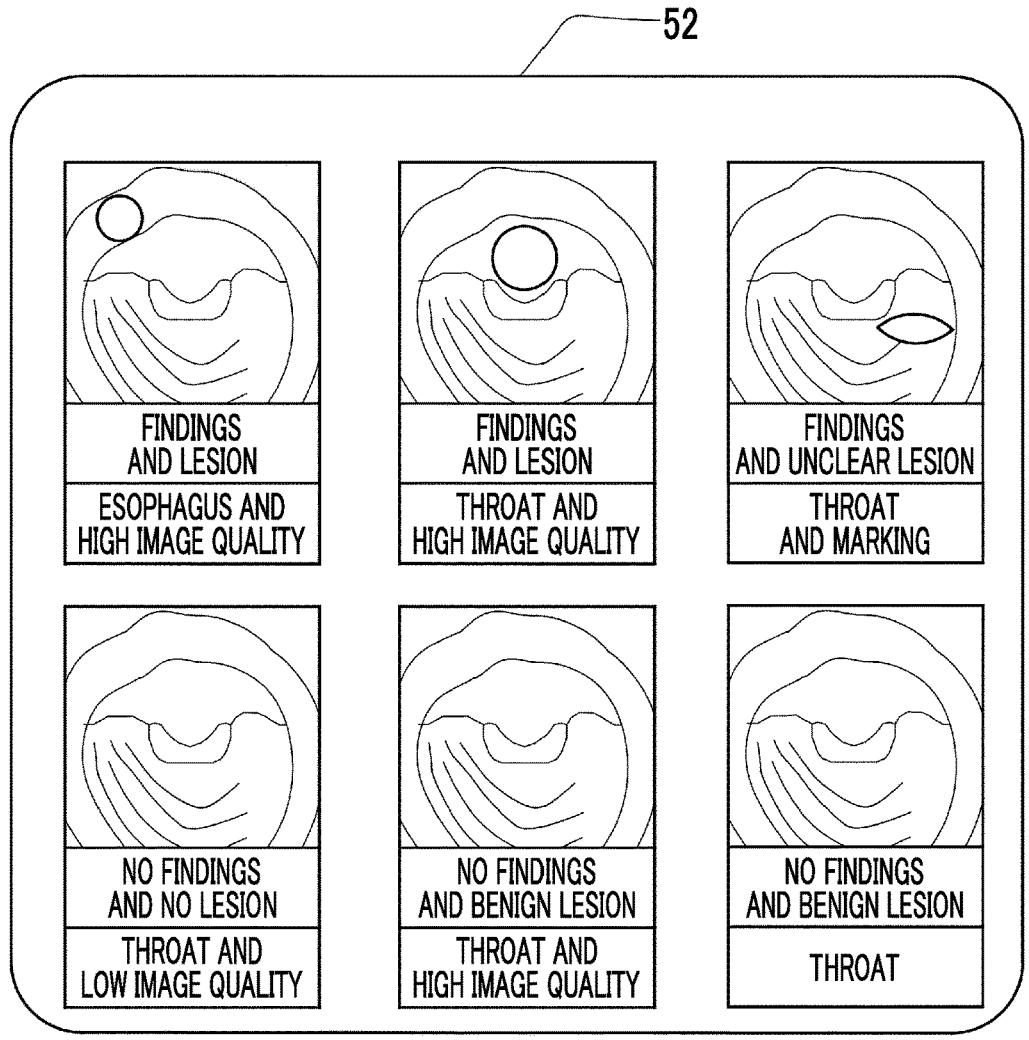
FIG. 12 is an explanatory diagram of sorting out the training data based on image information.
Figure 12:
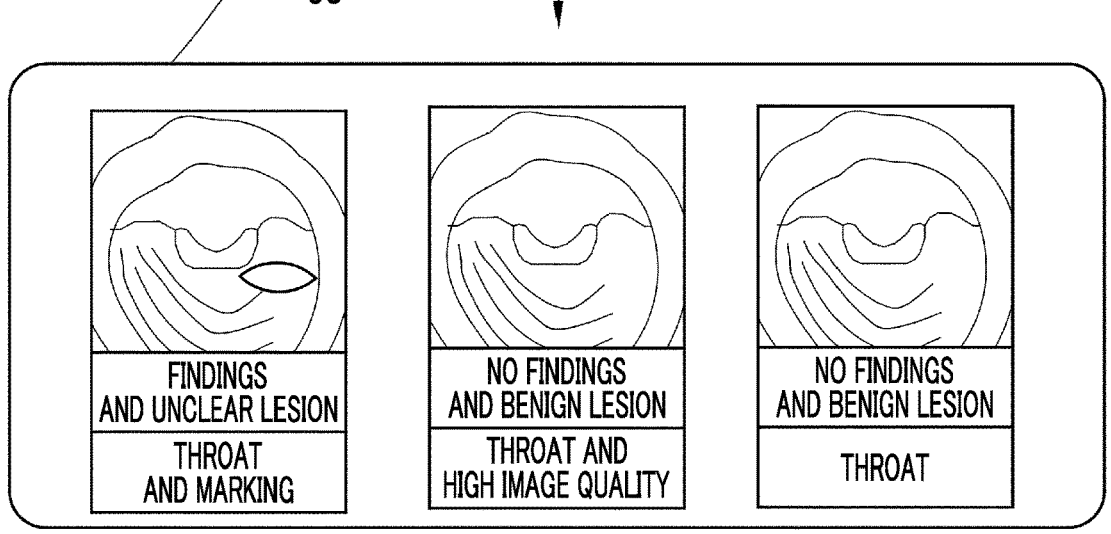

As shown in FIG. 12, in a case of sorting by image information, a normal image that does not have a lesion or a benign lesion and has a common point with the standard image 50 in the image information is sorted out as the training data 53. In addition to lesion information and findings information, site and organ information, image quality information, a treatment method, and a specific keyword are used in sorting out the training data 53. The image quality information is information related to the presence or absence of blur or blurriness and resolution, the site and organ information refers to whether a place of which an image is picked up is any one of the oral cavity, throat, stomach, small intestine, or large intestine, and the treatment method is information related to treatment such as ablation, excision, hemostasis, and marking performed in the past in a case where a treatment mark is included. In addition, the specific keyword is information indicating that the image is a normal image, such as keywords including "no lesion", "normal", and "no abnormal findings" of findings.

Figure 13:
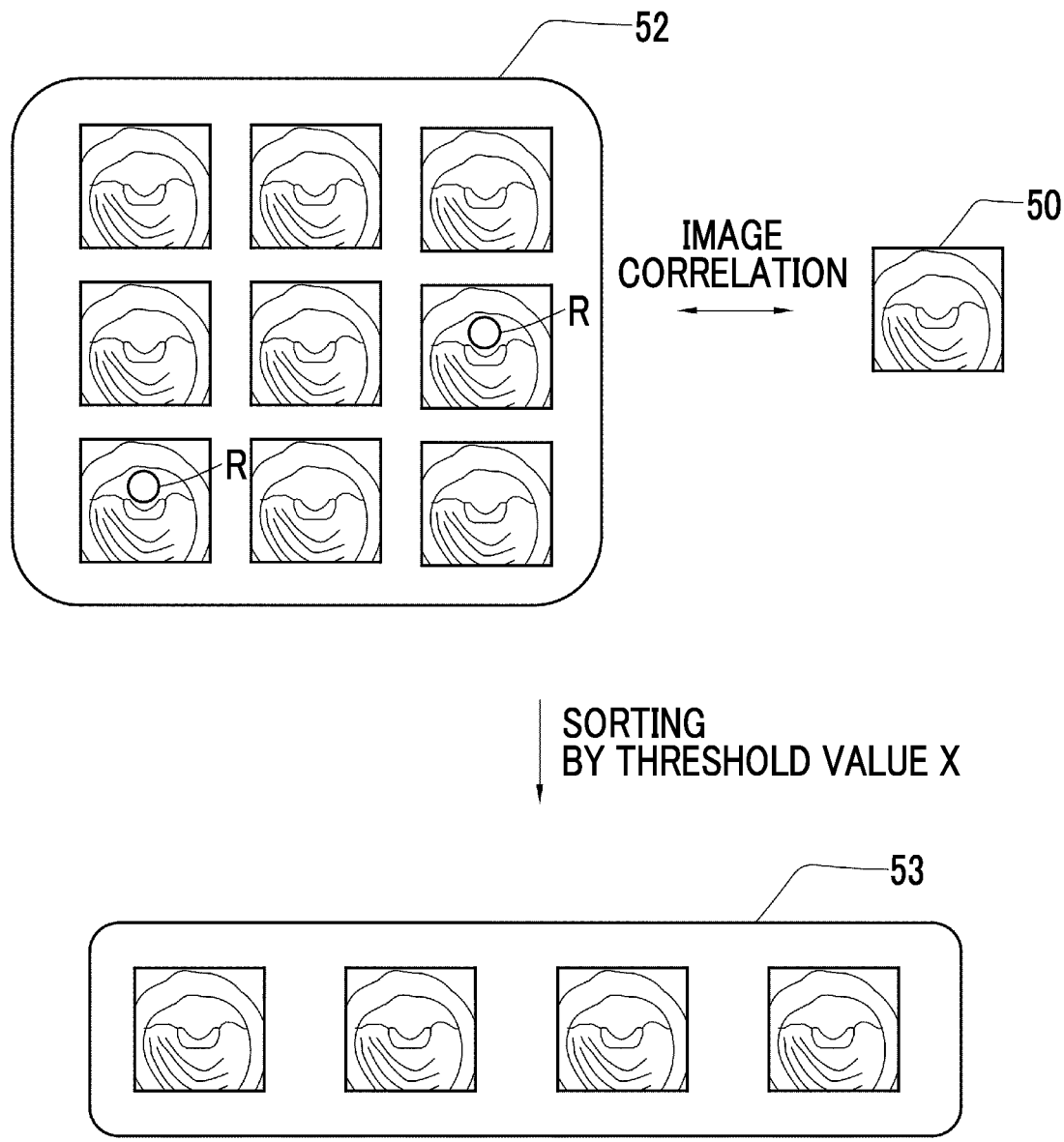
FIG. 13 is an explanatory diagram of sorting out the training data based on image correlation with the standard image.

As shown in FIG. 13, the training data 53 is sorted out through a method using an image correlation method. A correlation value is calculated by comparing the standard image 50 and each image of the learning candidate data set 52 with each other. An image exceeding a previously set threshold value is sorted out as the training data 53 using the correlation value of the image compared with the standard image 50. For example, in a case where an image correlation value with respect to one standard image 50 is acquired for nine images configuring the learning candidate data set 52 in a state where a threshold value X is set, an image having more common points or similarities to the standard image 50 has a higher image correlation value. On the contrary, in a case where there are many differences from the standard image 50, which is a normal image, such as an image having the region-of-interest R or a case where there are few common points and similarities, the image correlation value decreases. Although four images are sorted out as the training data 53 in the example of the threshold value X, in a case where the threshold value is a different value, the number of images can be increased or decreased accordingly. The threshold value in image correlation can be set to any value. In a case of setting the threshold value, it is preferable to set according to imaging conditions such as an imaging speed. The set threshold value is a value at which an image having at least the region-of-interest R is not sorted out.

Figure 14:
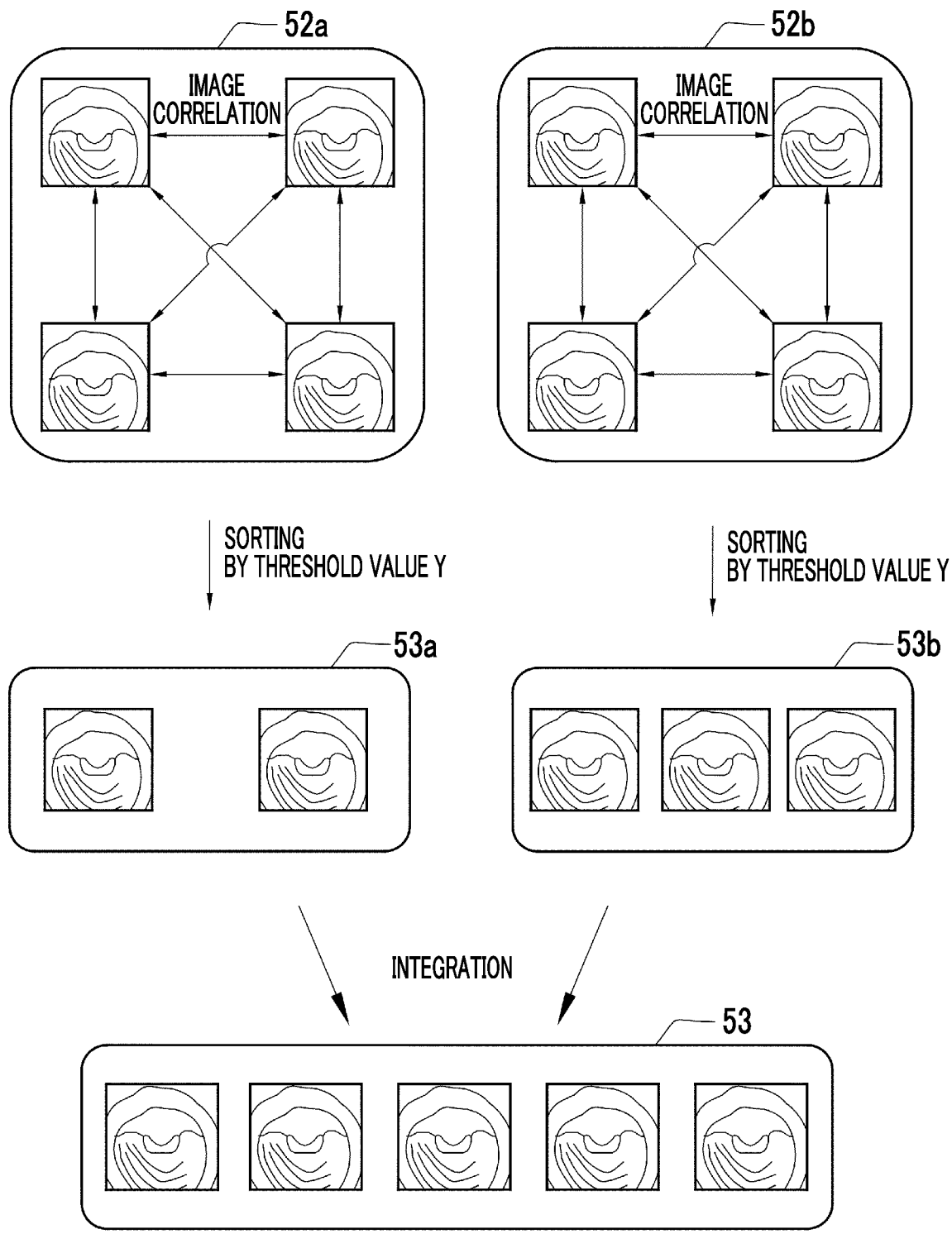
FIG. 14 is an explanatory diagram of sorting out the training data based on the image correlation without using the standard image.

As shown in FIG. 14, in sorting in the image correlation method, the training data 53 can be sorted out from images included in the learning candidate data set 52 in the image correlation method instead of sorting in which the standard image 50 is used. In this case, since a load from calculating a correlation value is larger than the image correlation method performed on one or multiple standard images 50, it is preferable to perform sorting in the image correlation method by dividing into a plurality of groups. For example, in a learning candidate data set 52a, six image correlation values are calculated for four images. An average value of image correlation values related to each image is acquired, sorting is performed according to a previously set threshold value Y using the average value. As a result of sorting by the threshold value Y, two images are sorted out as training data 53a. Similarly, in a learning candidate data set 52b, six image correlation values are calculated for four images, and training data 53b is sorted out from the average value of each image according to the threshold value Y. As a result of sorting by the threshold value Y, three images are sorted out as training data 53b. The training data 53a and the training data 53b obtained by sorting are integrated as the training data 53. A division method may be random, or division may be performed according to imaging conditions. A range of the threshold value of the correlation value, which is a sorting target as the training data 53 according to the division method, may be changed.

For example, in a case where an imaging speed is approximately equal to or lower than an average, images are randomly divided or are divided such that the images have many common points such as image information, and it is preferable to sort out, as the training data 53, an image that has a correlation value, which is calculated in image correlation between images of the learning candidate data sets 52a and 52b and is equal to or larger than a certain value.

In addition, in a case where the imaging speed is high and a change between frames is large, images having similar imaging times may be grouped as the learning candidate data set 52a. In this case, an image that has a correlation value, which is calculated in image correlation with respect to a peripheral frame image and is equal to or smaller than a certain value, is sorted out as the training data 53. In order to prevent an image having a low image quality from being added, narrowing down by image information may be simultaneously performed.

Figure 15:
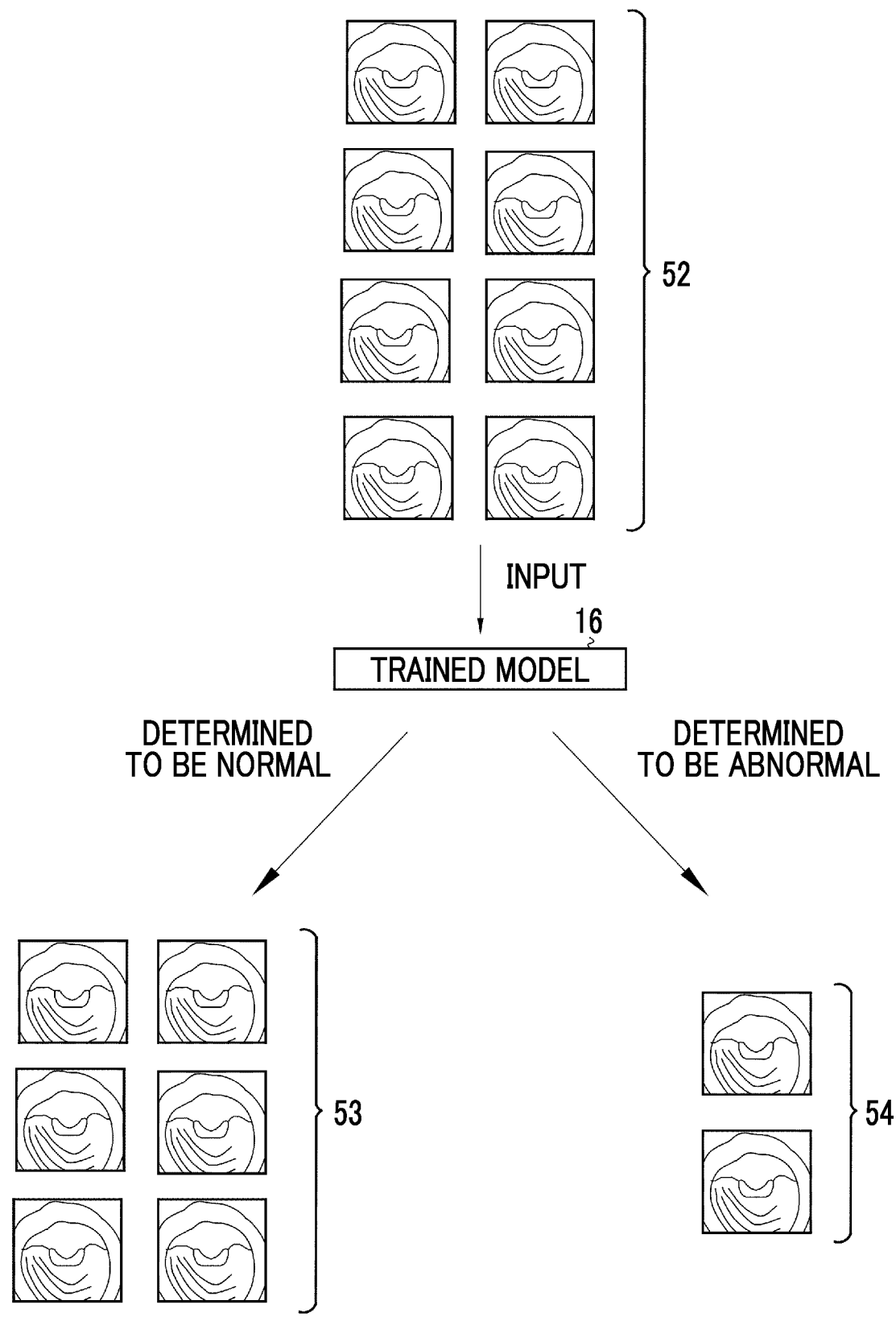
FIG. 15 is an explanatory diagram of sorting out the training data using the inference result of the machine learning.

As shown in FIG. 15, the training data 53 may be sorted out from an inference result of machine learning in which the trained model 16 connected to the learning device 11 is used. Learning related to a normal image is previously performed, and inference is made to infer whether or not an image is normal. Based on the inference result, an image determined to be normal is sorted out as the training data 53. An image which is determined to be abnormal or is determined to be not normal is the non-adopted image 54 and is not used thereafter.

Figure 16:
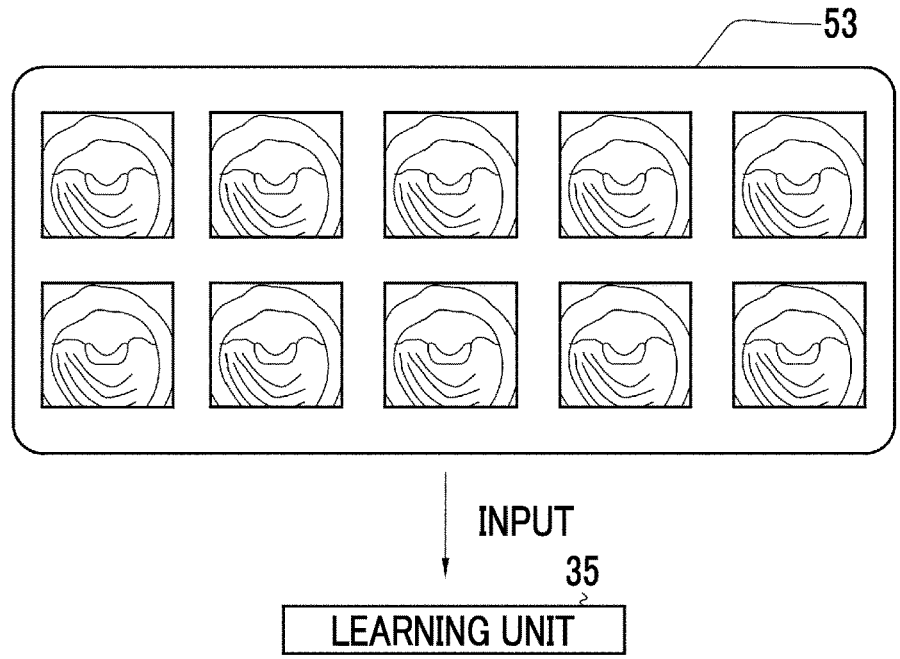
FIG. 16 is an explanatory diagram of performing learning by inputting the training data into a learning unit.

As shown in FIG. 16, the learning unit 35 performs learning using the training data 53. The learning unit 35 comprises a learning model. Specifically, the learning unit performs machine learning of inputting an image configuring the training data 53 into the learning model. A trained model created through machine learning is stored in the storage memory 24 or is transmitted to an external device such as the database 12 and is stored. In a case the amount of the training data 53 is small, it is preferable to perform sorting again under the same conditions and to acquire the training data 53.

The learning model performs machine learning. For example, the learning model is a computer algorithm that consists of a neural network, classifies a still image group or a moving image input according to learning content, and infers detection of a specific image. A learning method in machine learning includes learning of a self-encoder, learning of a generative adversarial network (GAN), and learning of an image interpolator. It is preferable to store the training data 53 together with or separately from the created trained model after learning so that the training data can be used in another learning.

The self-encoder uses an intermediate feature amount calculated by encoding an image or a restoration error in a case of restoration after encoding. The GAN is also called a hostile generation network, generates a non-existent image using a discriminator and a generator, and in a case of being used as an abnormality detector, performs abnormality detection with the discriminator and abnormality detection with the generator. The GAN may be an abnormality detector obtained by combining the discriminator and the generator. The image interpolator uses a restoration error of a randomly deleted image region.

Figure 18:
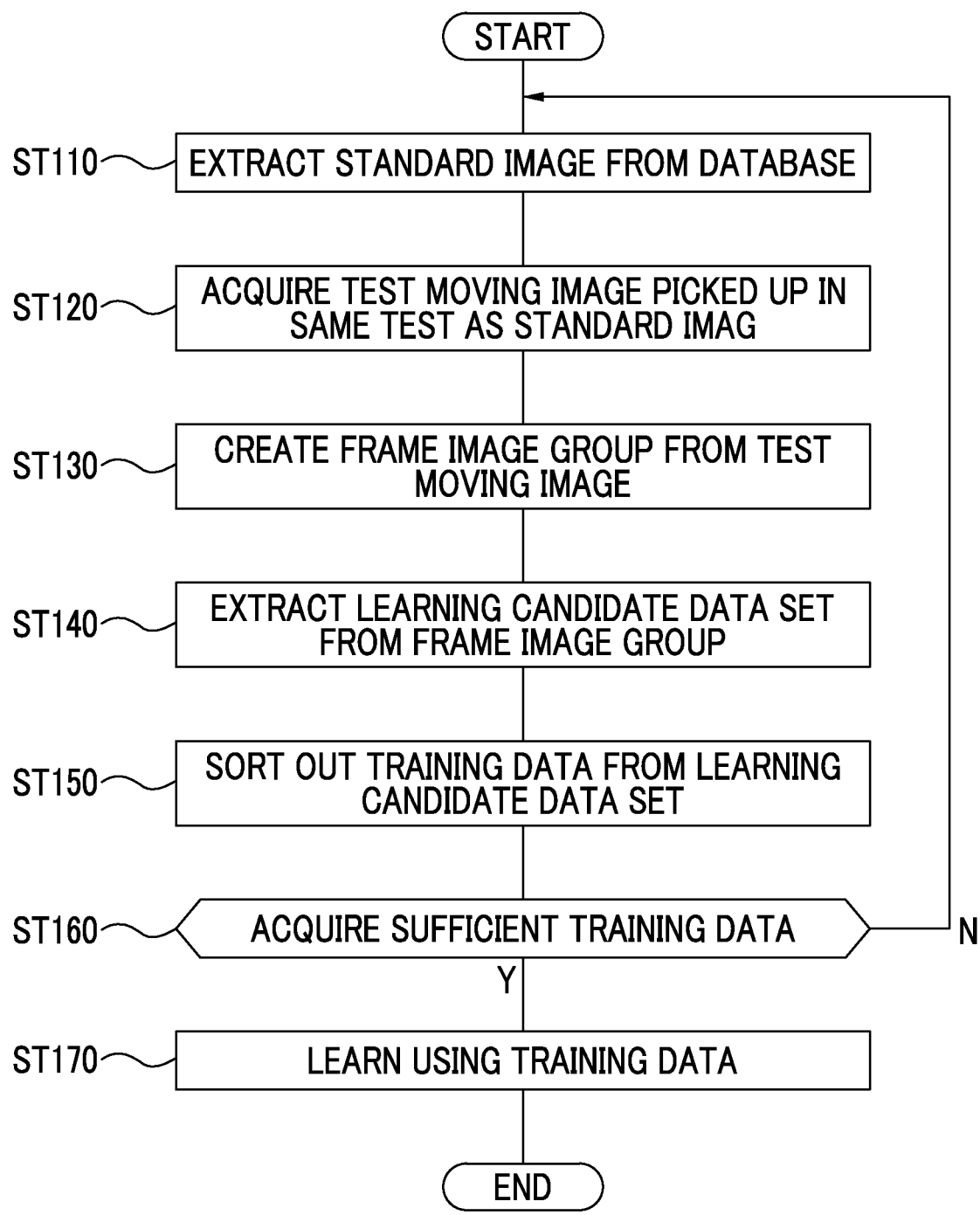
FIG. 18 is a flowchart showing the series of flows of the present invention.

Next, the series of flows of operations in which the learning device of the present embodiment is used will be described along a flowchart shown in FIG. 18. The learning device 11 extracts the standard image 50 from the database 12 that stores a still image or a moving image in a medical test (Step ST110). The test moving image 44 picked up in the same test as the standard image 50 is acquired based on a test ID or a patient ID of the extracted standard image 50 (Step ST120). An image group in a necessary range is extracted from the acquired test moving image 44, and the frame image group 51 is created (Step ST130). An image group picked up within a time range determined in advance with an imaging time of the standard image 50 as reference is extracted from the frame image group 51 as the learning candidate data set 52 (Step ST140). Based on image information of the standard image 50, a normal image is sorted out from the extracted learning candidate data set 52 as the training data 53 (Step ST150). As a result of sorting, in a case where the training data 53 is sufficiently acquired (Y in Step ST160), the training data 53 is learned, and machine learning such as generation of a trained model is performed (Step ST170). As a result of sorting, in a case where the training data 53 is not sufficiently acquired (N in Step ST160), the learning device 11 again extracts the standard image 50 from the database 12 (Step ST110) and collects the training data 53.

The present invention is the learning device 11 that learns the training data 53 which is sorted out, but may be used as a medical image processing terminal device that stores or transmits the training data 53 to other medical devices without performing learning. The training data 53 acquired by the training data sorting unit 34 is stored in the database 12 or is temporarily stored in the storage memory 24 instead of being transmitted to the learning unit 35.

Although an example in which the database 12, to which the learning device 11 is connected, is connected to the endoscope system 13, and an endoscope test motion picture acquired by the endoscope 13a is processed has been described in the present embodiment, the present invention is not limited thereto, and image sorting may be performed on a motion picture or a still image group acquired by other medical devices such as an ultrasound image imaging device and a radiation imaging device to perform learning.

In the embodiment, hardware structures of processing units that perform various types of processing, including the standard image acquisition unit 31, the frame image group creation unit 32, the learning candidate data set extraction unit 33, the training data sorting unit 34, and the learning unit 35 included in the central control unit 20, the image acquisition unit 21, the output control unit 22, the input reception unit 23, and the training data management unit 30, are various types of processors as follows. The various types of processors include a central processing unit (CPU) that is a general-purpose processor which executes software (program) and functions as various types of processing units, a programmable logic device (PLD) that is a processor of which a circuit configuration can be changed after manufacturing a field programmable gate array (FPGA), and a dedicated electric circuit that is a processor having a dedicated circuit configuration designed to execute various types of processing.

One processing unit may be composed of one of the various types of processors, or may be composed of the same type or different types of two or more processors (for example, a plurality of FPGAs or a combination of a CPU and an FPGA). In addition, one processor may configure a plurality of processing units. As an example of configuring a plurality of processing units with one processor, first, there is a form in which one processor is configured by a combination of one or more CPUs and software and the processor functions as the plurality of processing units, as represented by a computer such as a client and a server. Second, there is a form in which a processor that realizes functions of the entire system including the plurality of processing units with one integrated circuit (IC) chip is used, as represented by a system on chip (SoC). As described above, the various types of processing units are composed of one or more of the various types of processors used as a hardware structure.

Further, the hardware structure of the various types of processors is, more specifically, an electric circuit (circuitry) in a form in which circuit elements such as semiconductor elements are combined. In addition, a hardware structure of the storage unit is a storage device such as a hard disc drive (HDD) and a solid state drive (SSD).

EXPLANATION OF REFERENCES

10: learning system
11: learning device
12: database
13: endoscope system
13a: endoscope
14: display
15: user interface
16: trained model
20: central control unit
21: image acquisition unit
22: output control unit
23: input reception unit
24: storage memory
30: training data management unit
31: standard image acquisition unit
32: frame image group creation unit
33: learning candidate data set extraction unit
34: training data sorting unit
35: learning unit
40: medical test report
41: diagnosis image
42: report-published image
42a: report-published image
43: report-non-published image
44: test moving image
49: database stored image group
50: standard image
51: frame image group
52: learning candidate data set
52a: learning candidate data set
52b: learning candidate data set
53: training data
53a: training data
53b: training data
54: non-adopted image
60: image display region
61: image information display field 62: adoption button
63: non-adoption button
64: image selection region
65: image display region
66: scroll bar
R: region-of-interest

What is claimed is:

1. A learning device comprising:
a processor configured to:
   extract a standard image from a still image group or a moving image associated with medical test report data stored in a database, using the medical test report data;
   sort out training data from a frame image group configuring the still image group or the moving image associated with the medical test report data, using the standard image; and
   perform learning using the training data,
wherein the processor is configured to:
   extract a learning candidate data set from the standard image, and sort out the training data from the learning candidate data set;
   extract, as the learning candidate data set, an image group acquired within a predetermined time range from a time at which the standard image is acquired, from the frame image group configuring the still image group or the moving image associated with the medical test report data; and
   sort out, as the training data, at least any one of an image including the same site, an image including the same organ, an image having image correlation which is equal to or larger than a certain value, or an image having the same inference result of machine learning, with respect to the standard image from the learning candidate data set.

2. The learning device according to claim 1,
wherein the processor is configured to extract the standard image based on lesion information from the still image group or the moving image associated with the medical test report data.

3. The learning device according to claim 2,
wherein the processor is configured to extract at least any one of an image without findings of the medical test report data, an image that does not have a lesion, or an image of a benign lesion, as the standard image.

4. The learning device according to claim 1,
wherein the processor is configured to extract, from the still image group or the moving image associated with the medical test report data, the standard image based on at least any one of lesion information, findings information, image quality information, site information, organ information, a treatment method, or a specific keyword, which is information linked with the medical test report data.

5. The learning device according to claim 1,
wherein the processor is configured to input the still image group or the moving image associated with the medical test report data into a trained model, and extract the standard image using an inference result of machine learning in which the trained model is used.

6. The learning device according to claim 1,
wherein the processor is configured to display, on a display, at least any one of the still image group or the moving image associated with the medical test report data, and extract the standard image by user selection.

7. The learning device according to claim 1,
wherein the processor is configured to sort out, as the training data, an image that does not have a lesion or an image of a benign lesion from the learning candidate data set using the standard image.

8. The learning device according to claim 1,
wherein the processor is configured to sort out, as the training data, an image that has image correlation, which is equal to or smaller than a certain value, with respect to a peripheral frame image instead of sorting out using the standard image from the learning candidate data set.

9. An operation method of a learning device comprising:
extracting a standard image from a still image group or a moving image associated with medical test report data stored in a database, using the medical test report data;
sorting out training data from a frame image group configuring the still image group or the moving image associated with the medical test report data, using the standard image; and
performing learning using the training data,
wherein the method further comprises:
   extracting a learning candidate data set from the standard image, and sorting out the training data from the learning candidate data set;
   extracting, as the learning candidate data set, an image group acquired within a predetermined time range from a time at which the standard image is acquired, from the frame image group configuring the still image group or the moving image associated with the medical test report data; and
   sorting out, as the training data, at least any one of an image including the same site, an image including the same organ, an image having image correlation which is equal to or larger than a certain value, or an image having the same inference result of machine learning, with respect to the standard image from the learning candidate data set.

10. A medical image processing terminal comprising:
a processor configured to:
   extract a standard image from a still image group or a moving image associated with medical test report data stored in a database, using the medical test report data; and
   sort out training data from a frame image group configuring the still image group or the moving image associated with the medical test report data, using the standard image, and store the training data,
wherein the processor is configured to:
   extract a learning candidate data set from the standard image, and sort out the training data from the learning candidate data set;
   extract, as the learning candidate data set, an image group acquired within a predetermined time range from a time at which the standard image is acquired, from the frame image group configuring the still image group or the moving image associated with the medical test report data; and
   sort out, as the training data, at least any one of an image including the same site, an image including the same organ, an image having image correlation which is equal to or larger than a certain value, or an image having the same inference result of machine learning, with respect to the standard image from the learning candidate data set.

* * * * *